(12) United States Patent
Weitzner

(10) Patent No.: US 9,044,240 B2
(45) Date of Patent: Jun. 2, 2015

(54) HEMOSTASIS CLIP

(75) Inventor: Barry Weitzner, Acton, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 375 days.

(21) Appl. No.: 13/032,898

(22) Filed: Feb. 23, 2011

(65) Prior Publication Data

US 2011/0224706 A1    Sep. 15, 2011

Related U.S. Application Data

(60) Provisional application No. 61/312,360, filed on Mar. 10, 2010.

(51) Int. Cl.
| | |
|---|---|
| *A61B 17/10* | (2006.01) |
| *A61B 17/128* | (2006.01) |
| *A61B 17/122* | (2006.01) |
| *A61B 17/08* | (2006.01) |
| *A61B 17/12* | (2006.01) |
| *A61B 19/00* | (2006.01) |

(52) U.S. Cl.
CPC ............ *A61B 17/1285* (2013.01); *A61B 17/083* (2013.01); *A61B 2017/12004* (2013.01); *A61B 17/122* (2013.01); *A61B 2019/307* (2013.01)

(58) Field of Classification Search
CPC ............. A61B 17/1285; A61B 17/122; A61B 17/1227; A61B 17/083; A61B 2017/12004
See application file for complete search history.

(56) References Cited

U.S. PATENT DOCUMENTS

| | | | |
|---|---|---|---|
| 4,627,444 A | 12/1986 | Brooker | |
| 4,733,664 A | 3/1988 | Kirsch et al. | |
| 5,049,153 A | 9/1991 | Nakao et al. | |
| 5,156,609 A | 10/1992 | Nakao et al. | |
| 6,808,491 B2 | 10/2004 | Kortenbach et al. | |
| 6,814,742 B2 * | 11/2004 | Kimura et al. | 606/151 |
| 6,824,548 B2 | 11/2004 | Smith et al. | |
| 6,945,979 B2 | 9/2005 | Kortenbach et al. | |
| 6,991,634 B2 | 1/2006 | Sugiyama et al. | |
| 7,011,667 B2 * | 3/2006 | Kobayashi et al. | 606/142 |
| 7,070,602 B2 | 7/2006 | Smith et al. | |
| 7,094,245 B2 * | 8/2006 | Adams et al. | 606/142 |

(Continued)

FOREIGN PATENT DOCUMENTS

| | | |
|---|---|---|
| JP | 2005 135 39 | 1/2005 |
| WO | 03/088850 | 10/2003 |
| WO | 2008/070486 | 6/2008 |

*Primary Examiner* — Elizabeth Houston
*Assistant Examiner* — Todd J Scherbel
(74) *Attorney, Agent, or Firm* — Fay Kaplun & Marcin, LLP

(57) ABSTRACT

A device for clipping tissue includes a clip including first and second arms coupled to one another and biased toward an open configuration and a core member including a proximal portion and a distal portion connected to one another via a frangible link configured to break when subjected to a predetermined tension, the distal end of the core member being directly coupled to the first arm. The device further includes a capsule slidably housing the distal end of the core member and a proximal portion of the clip, the capsule being dimensioned so that, when the clip is drawn proximally thereto, contact between the arms and the capsule move the arms toward one another into a closed, tissue-gripping configuration, the core member and the capsule being longitudinally movable relative to one another to move the clip between and a closed tissue-gripping configuration and the open configuration.

6 Claims, 2 Drawing Sheets

(56) References Cited

U.S. PATENT DOCUMENTS

| | | |
|---|---|---|
| 7,122,041 B2 | 10/2006 | Surti |
| 7,223,271 B2 | 5/2007 | Muramatsu et al. |
| 7,452,327 B2 * | 11/2008 | Durgin et al. ............... 600/104 |
| 7,727,247 B2 * | 6/2010 | Kimura et al. ............... 606/157 |
| 8,152,822 B2 * | 4/2012 | Gayzik ......................... 606/151 |
| 8,162,959 B2 * | 4/2012 | Cohen et al. ................. 606/142 |
| 2004/0176784 A1 * | 9/2004 | Okada .......................... 606/142 |
| 2005/0182426 A1 | 8/2005 | Adams et al. |
| 2006/0100645 A1 * | 5/2006 | Kobayashi et al. .......... 606/142 |
| 2006/0190015 A1 * | 8/2006 | Matsuno et al. .............. 606/142 |
| 2006/0224165 A1 | 10/2006 | Surti et al. |
| 2007/0282353 A1 | 12/2007 | Surti |
| 2007/0282355 A1 | 12/2007 | Brown et al. |
| 2007/0293875 A1 | 12/2007 | Soetikno et al. |
| 2008/0140089 A1 * | 6/2008 | Kogiso et al. ................ 606/142 |
| 2008/0306491 A1 * | 12/2008 | Cohen et al. ................. 606/142 |
| 2010/0152753 A1 * | 6/2010 | Menn et al. .................. 606/158 |
| 2011/0196390 A1 * | 8/2011 | Kogiso et al. ................ 606/151 |
| 2011/0245855 A1 * | 10/2011 | Matsuoka et al. ............ 606/157 |

* cited by examiner

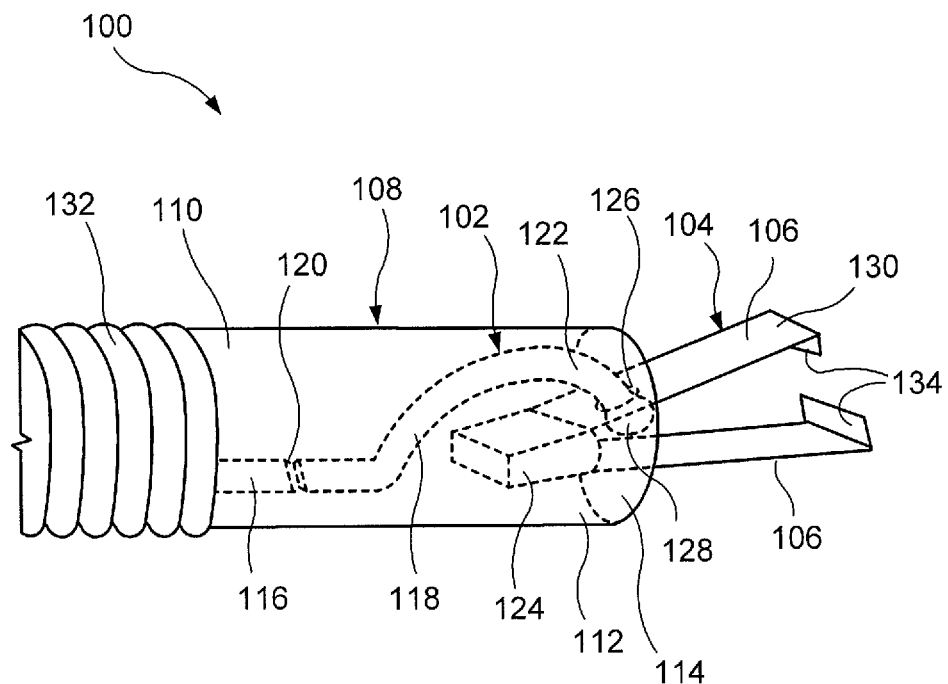
F I G. 1
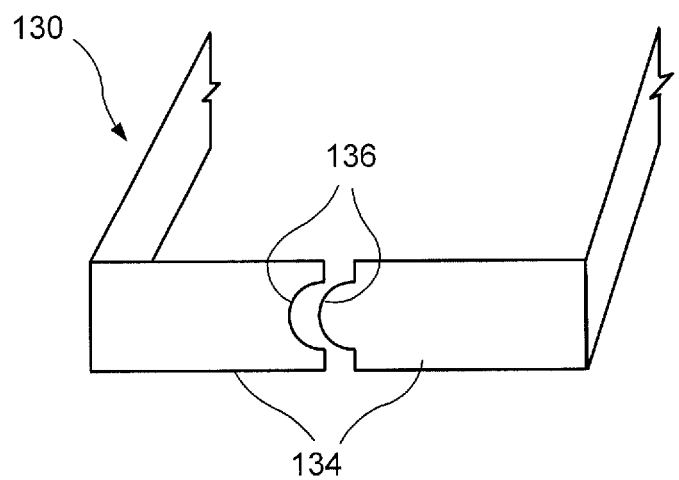
F I G. 2

HEMOSTASIS CLIP

PRIORITY CLAIM

This application claims the priority to the U.S. Provisional application Ser. No. 61/312,360, entitled "Endoscope Anchoring Device" filed Mar. 10, 2010. The specification of the above-identified application is incorporated herewith by reference.

BACKGROUND

Pathologies of the gastrointestinal system, the biliary tree, the vascular system and other body lumens and hollow organs are often treated through endoscopic procedures, many of which require active and/or prophylactic hemostasis to control internal bleeding. Tools for deploying hemostatic clips via an endoscope are often used to stop internal bleeding by clamping together the edges of the wounds or incisions. Hemostasis clips grasp tissue surrounding a wound and hold edges of the wound together by applying pressure to the site to allow natural healing processes to close the wound. Specialized endoscopic clipping devices are used to deliver the clips to the desired locations within the body and to position and deploy the clips at the desired locations after which the clip delivery device is withdrawn, leaving the clip within the body. These clips may be left in place until they are sloughed off through natural processes or removed later through a separate procedure after the bleeding site has healed.

SUMMARY OF THE INVENTION

The present invention is directed to a device for clipping tissue, comprising a clip including first and second arms coupled to one another and biased toward an open configuration in which distal ends of the first and second arms are separated from one another and a core member including a proximal portion and a distal portion connected to one another via a frangible link configured to break when subjected to a predetermined tension, the distal end of the core member being directly coupled to the first arm in combination with a capsule slidably housing the distal end of the core member and a proximal portion of the clip, the capsule being dimensioned so that, when the clip is drawn proximally thereinto, contact between the arms and the capsule move the arms toward one another into a closed, tissue-gripping configuration, the core member and the capsule being longitudinally movable relative to one another to move the clip between and a closed tissue-gripping configuration and the open configuration.

BRIEF DESCRIPTION OF THE DRAWINGS

FIG. 1 shows a perspective view of a clipping device according to a first exemplary embodiment of the present invention;

FIG. 2 shows a perspective view a distal end of a clip of the clipping device of FIG. 1;

DETAILED DESCRIPTION

Figure 3:
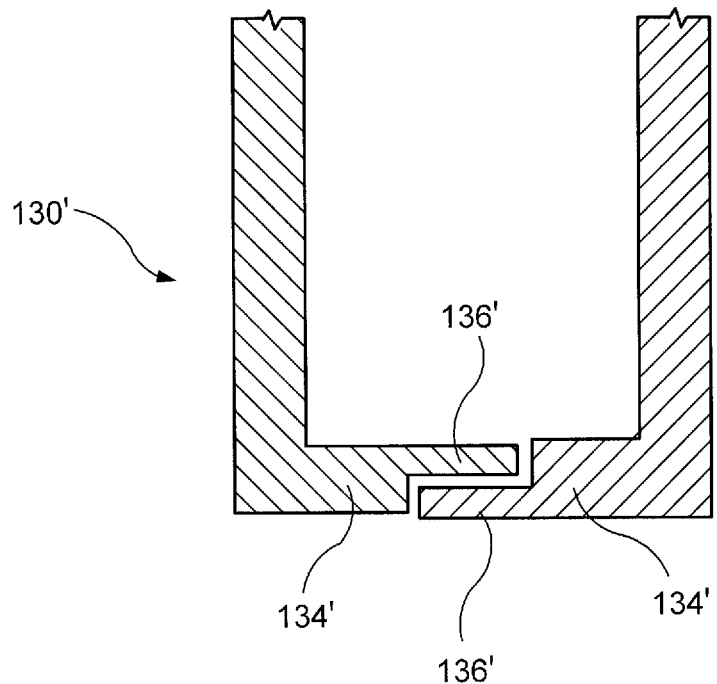
FIG. 3 shows a side view of a distal end of a clip according to an alternate embodiment of the present invention.

The present may be further understood with reference to the following description and the appended drawings, wherein like elements are referred to with the same reference numerals. The present invention relates to devices for hemostatic clipping and, in particular, to a hemostatic clip that may be deployed in a single stage deployment process. Exemplary embodiments of the present invention provide a core member including a frangible link that is broken when a predetermined load is exceeded such that the clip may be deployed in the single stage process. These embodiments also relate to other types of clipping devices including, but not limited to, clips for fastening tissue layers together and clips for closing opening in one or more layers of tissue. For example, the clipping device may be used to close wounds and/or incisions for hemostasis of natural or surgical bleeding, "stitching" a wound, occluding a vessel or lumen, plicating a hollow organ, attaching tissues, tissue approximation, etc.

As shown in FIG. 1, a clipping device 100 according to a first exemplary embodiment of the present invention, comprises a core member 102 engaging a clip 104 including two or more arms 106 biased toward an open configuration, in which distal ends of the arms 106 are spaced apart from one another. The core member 102 is housed substantially within a capsule 108 such that the capsule 108 and the core member 102, along with the clip 104 engaged thereto, are movable relative to one another along a longitudinal axis of the clipping device 100 between the open tissue-receiving configuration and a closed tissue-gripping configuration, in which the distal ends 130 are moved toward one another to grip tissue therebetween. The distal ends 130 may include teeth and/or hooks 134 that extend radially inward to facilitate gripping of the tissue. For example, as shown in FIG. 2, the hooks 134 may be shaped to correspond to one another such that ends 136 of the hooks 134 are nested when moved toward one another. In another embodiment, as shown in FIG. 3, a distal end 130' may include hooks 134' with ends 136' that overlap to grip tissue therebetween. The arms 106 of the clip 104 may be formed of a variety of different types of material. For example, the arms 106 may be formed of spring materials and/or plastics such as nylon, polyoxymethylene plastic, PEEK, low density polyethylene (LDPE), etc. Alternatively, the arms 106 may be formed of metals such as elgiloy, steel, nitinol, titanium, etc. Additionally, the arms 106 may be formed of any bioabsorbable and/or biodegradable material.

Movement of the core member 102 and deployment of the clip 104 is facilitated by a deployment mechanism attached to a proximal end of the clipping device 100. The clip 104 may be deployed in a single stage deployment process substantially as described in U.S. patent application Ser. No. 12/107,559 entitled "Single Stage Hemostasis Clipping Device" to Cohen et al., the entire disclosure of which is incorporated herein by reference. Specifically, the capsule 108 may be coupled to a bushing (not shown) coupled to a handle via a flexible member 132 (e.g., a coil), allowing the handle to remain outside the body while the flexible member extends along a tortuous path within the body to the target location (e.g., via a body lumen accessed via a naturally occurring bodily orifice). The core member 102 may be, for example, a wire extending through the flexible member 132 connected between the clip 104 and an actuator on the handle (not shown) so that, movement of the actuator moves the core member 102 and the clip 104 proximally and distally relative to the capsule 108 as will be described below. Thus, longitudinal movement of the core member 102 relative to the capsule 108 and the flexible member 132 moves the clipping device 100 between the open and the closed configurations.

The capsule 108 extends longitudinally from a proximal end 110 to a distal end 112 and includes a lumen 114 extending therethrough for housing a distal end of the core member 102 and at least a proximal portion of the clip 104. Drawing the core member 102 proximally relative to the capsule 108 draws the clip 104 proximally into the capsule 108 so that the capsule 108 progressively covers the arms 106 of the clip 104 forcing the arms 106 toward one another into the closed configuration. Subsequently, the core member 102 may be moved distally relative to the capsule 108 to move the clip 104 distally out of the capsule 108 uncovering the arms 106 so that they revert to the open configuration under their inherent bias.

The core member 102 includes a proximal portion 116 coupled to a distal portion 118 via a frangible link 120 designed to fail when subjected to a predetermined tension. The distal portion 118 may be housed substantially within the capsule 108 while the proximal portion 116 extends proximally therefrom and through the flexible member 132. It will be understood by those of skill in the art that the frangible link 120 may be formed as a weld or other suitable connection so long as the connection remains in place until subjected to a tension of at least a predetermined magnitude and fails when a load of this magnitude is applied. It will also be understood by those of skill in the art that the proximal portion 116 and the distal portion 118 may be two distinct elements with the frangible link 120 formed as a connection point therebetween. The proximal and distal portions 116, 118 may be welded, glued or bonded to one another via any other material designed to break when subjected to a tension of at least the predetermined magnitude. Alternatively, the proximal and distal portions 116, 118 may be connected to one another by one or more mechanical connectors designed to break when subjected to a tension of at least the predetermined magnitude or may simply be a weakened portion of the core member 102 configured to fail when subjected to the predetermined tension. The core member 102 may be formed of plastics such as, for example, polycarbonate resin thermoplastics and LDPE, or metals such as steel, aluminum and nitinol.

A distal end 122 of the distal portion 118 engages a proximal end 124 of the clip 104. The arms 106 of the clip 104 may be coupled to one another at the proximal end 124. Thus, the distal end 122 of the core member 102 may engage only one of the arms 106, while still providing a force to the entire clip 104 so that movement of the core member 102 moves both arms 106 while it engages only one of the arms 106. The distal end 122 of the core member 102 may be curved and substantially hook-shaped such that the distal end 122 is receivable within an opening 126 in one of the arms 106 at the proximal end 124 thereof. The distal end 122 may also include a retaining element 128 at an end thereof to prevent the distal end 122 from becoming inadvertently disengaged from the arm 106. The retaining element 128 may comprise a tab, hook, ball or other mechanical lock to hold the core member 102 in connection with the arm 106. It will be understood by those of skill in the art, however, that the distal portion 118 of the core member 102 may be engaged to one of the arms 106 using any of a variety of attachment mechanisms so long as the distal portion 118 engages the arm 106 in a manner preventing the distal portion 118 from inadvertently disengaging from the arm 106.

In an exemplary technique according to the present invention, the clipping device 100 is inserted into the body in the closed configuration for ease of insertion and advanced to a position proximate a target portion of tissue to be clipped (e.g., via a body lumen). The clip 104 is then moved to the open configuration so that the target tissue is positioned between the arms 106. The clip 104 is then withdrawn proximally into the capsule to draw the arms 106 together over the target tissue gripping the tissue in the closed configuration. It will be understood by those of skill in the art, however, that the clip 104 may be repeatedly moved between the open and closed configurations as desired, until the target portion of tissue is gripped as desired between the arms 106. Once the target tissue is gripped as desired between the arms 106, the core member 102 is drawn proximally, urging the arms 106 further proximally into the capsule 108. As distal ends 130 of the arms 106 are wider than the proximal ends 124 thereof, the width of the arms 106 defines a maximum extent to which the arms 106 may be drawn proximally into the capsule 108. After this maximum extent has been reached, drawing the core member 102 is further proximally relative to the capsule 108 and the distal ends 130 of the arms 106, increases the tension on the core member 102 until this load reaches the predetermined tension. Once the predetermined tension is reached, the frangible link 120 breaks allowing the proximal portion 116 to move further proximally relative to the arms 106 and the distal portion 118, which remain within the capsule 108, freeing the capsule 108 and the clip 104 from the device 100 and leaving them locked in place gripping the target tissue. According to an alternative technique, the clip 104 may be similarly deployed by moving the capsule 108 distally relative to the clip 104, while holding the clip 104 steady via the proximal portion 116, until the predetermined tension is reached breaking the frangible link 120 and freeing the capsule 108 and the clip 104 from the device 100.

Figure 4:
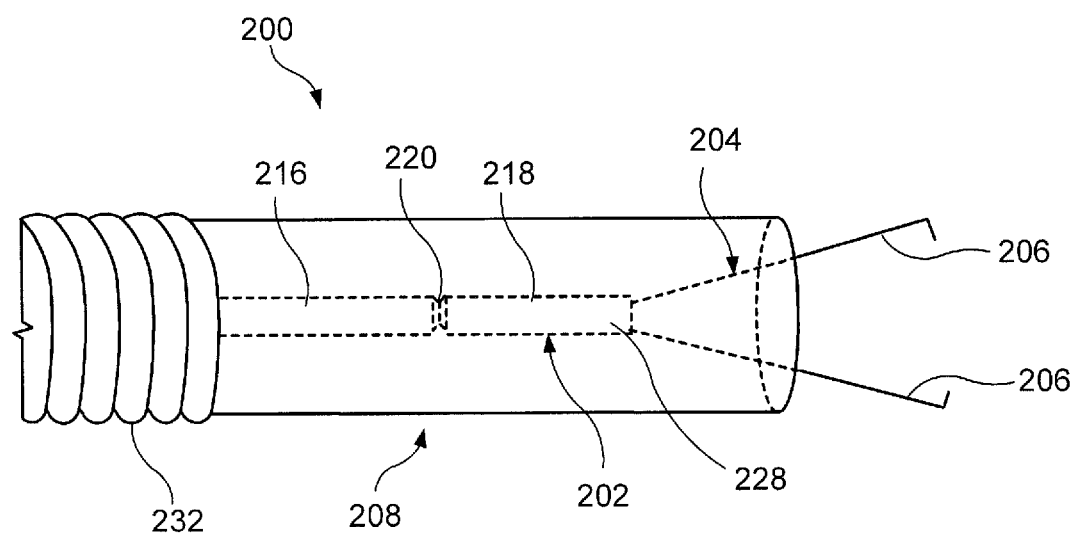
FIG. 4 shows a perspective view of a clipping device according to a second exemplary embodiment of the present invention.

As shown in FIG. 4, a device 200 according to a second exemplary embodiment of the present invention is substantially similar to the clipping device 100, and comprises a core member 202 attached to a clip 204 including at least two arms 206. As described in regard to the clipping device 100, the core member 202 (e.g., wire) includes a proximal portion 216 and a distal portion 218 connected to one another via a frangible link 220. The core member 202 is slidably housed within a capsule 208 connected to a handle (not shown) via a flexible member 232 such that the proximal portion 216 extends through the flexible member 232 to an actuator on the handle. The actuator moves the core member 202 longitudinally relative to the capsule 208 to move the clip 204 between an open, tissue receiving, configuration and a closed, tissue gripping, configuration.

The device 200, however, differs from the clipping device 100, in the attachment between the core member 202 and the clip 204. The distal portion 218 of the core member 202 is formed integrally with the arms 206 of the clip 204 such that the arms 206 extend distally from a distal end 228 of the distal portion 218. The distal portion 218 may be an extension of the arms 206 that is formed by twisting ends of the arms 206 together. Alternatively, the distal portion 218 may be a tubular element housing proximal ends of the arms 206 therewithin. The device 200 is utilized and deployed in substantially the same manner as described above in regard to the clipping device 100. In particular, the clip 204 is positioned adjacent a target portion of tissue and moved to the open configuration. The target portion of tissue is received between the arms 206 and the core member 202 is drawn proximally into the capsule 208 such that the arms 206 of the clip 204 are drawn together over the target tissue. Movement of the core member 202 further proximally, moves the arms 206 into the capsule 208 to a maximum extent. The application of additional proximally directed force to the core member 202 increases the tension in the core member 202 until the predetermined tension is reached, breaking the frangible link 220. The proximal portion 216 continues to move proximally relative to the arms 206 and the distal portion 218, which remain within the capsule 208, and the capsule 208 and the clip 204 are left deployed over the target tissue within the body.

It will be apparent to those skilled in the art that various modifications can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A device for clipping tissue, comprising:
   a clip including first and second arms coupled to one another and biased toward an open configuration in which distal ends of the first and second arms are separated from one another;
   a core member including a proximal portion and a distal portion connected to one another via a link configured to separate the proximal portion from the distal portion when subjected to a predetermined tension, a distal end of the core member being directly coupled to only the first arm; and
   a capsule slidably housing the distal end of the core member and a proximal portion of the clip, the capsule being dimensioned so that, when the clip is drawn proximally thereinto, contact between the arms and the capsule move the arms toward one another into a closed, tissue-gripping configuration, the core member and the capsule being longitudinally movable relative to one another to move the clip between the closed tissue-gripping configuration and the open configuration.

2. The device of claim 1, wherein the distal portion is hook-shaped with the distal end of the distal portion extending into an opening at a proximal end of the first arm.

3. The device of claim 2, wherein the distal portion includes a retaining element at an end thereof to prevent disengagement of the distal portion from the opening of the first arm.

4. The device of claim 1, wherein the distal end of the first arm includes a first gripping element extending radially inward toward the second arm to facilitate gripping of tissue therebetween.

5. The device of claim 4, wherein the distal end of the second atm includes a second gripping element extending radially inward toward the first arm to facilitate gripping of tissue therebetween.

6. A clipping device, comprising:
   a clip including first and second arms connected to one another at proximal ends thereof;
   a core member including a proximal portion and a distal portion connected to one another via a link constructed to separate the proximal portion from the distal portion when subjected to a predetermined load, the distal portion of the core member directly engaging the proximal end of only the first arm;
   a capsule slidably housing the core member and a proximal portion of the clip, the capsule and the core member being longitudinally movable relative to one another such that the clip is movable between an open tissue-receiving configuration and a closed tissue-gripping configuration; and
   a deployment mechanism including an actuator connected to the proximal portion of the core member to move the core member and the clip relative to the capsule.

* * * * *